US005194424A

United States Patent [19]

Malabarba et al.

[11] Patent Number: 5,194,424

[45] Date of Patent: Mar. 16, 1993

[54] $C^{63}$-AMIDE DERIVATIVES OF 34-DE(ACETYLGLUCOSAMINYL)-34-DEOXY-TEICOPLANIN AND THEIR USE AS MEDICAMENTS AGAINST BACTERIA RESISTANT TO GLYCOPEPTIDE ANTIBIOTICS

[75] Inventors: Adriano Malabarba, Binasco; Jürgen K. Kettenring, Varese, both of Italy

[73] Assignee: Gruppo Lepetit SpA, Milan, Italy

[21] Appl. No.: 887,121

[22] Filed: May 20, 1992

Related U.S. Application Data

[63] Continuation of Ser. No. 544,719, Jun. 27, 1990, abandoned, which is a continuation-in-part of Ser. No. 453,649, Dec. 20, 1989, abandoned.

[30] Foreign Application Priority Data

Dec. 27, 1988 [EP] European Pat. Off. ........ 88121708.7
May 28, 1990 [EP] European Pat. Off. ........ 90110102.2

[51] Int. Cl.[5] ........................ A61K 37/02; C07K 7/50; C07K 9/00

[52] U.S. Cl. ........................................... 514/8; 514/9; 530/317; 530/322; 530/323

[58] Field of Search ............... 530/317, 322, 345, 323; 514/8, 9

[56] References Cited

U.S. PATENT DOCUMENTS

| | | | |
|---|---|---|---|
| 4,542,018 | 9/1985 | Borghi et al. | 424/119 |
| 4,638,047 | 1/1987 | Szelke et al. | 530/332 |

*Primary Examiner*—Y. Christina Chan
*Attorney, Agent, or Firm*—John J. Kolano

[57] ABSTRACT

$C^{63}$-Amide derivatives of 34-de(acetylglucosaminyl)-34-deoxy-teicoplanin wherein the amide moiety is derived from a di- or poly-amine. The derivatives are prepared by reacting 34-de(acetylglucosaminyl)- 34-deoxy-teicoplanins with an active esters forming reagent such as chloroacetonitrile and then contacting the resulting active esters with the appropriate di- or polyamine. The amide derivatives which are active against Gram-positive microorganisms, in particular against Group A Streptococci were found to be active also against bacteria which are resistant to glycopeptide antibiotics.

13 Claims, No Drawings

$C^{63}$-AMIDE DERIVATIVES OF 34-DE(ACETYLGLUCOSAMINYL)-34-DEOXY-TEICOPLANIN AND THEIR USE AS MEDICAMENTS AGAINST BACTERIA RESISTANT TO GLYCOPEPTIDE ANTIBIOTICS

This application is a continuation of application Ser. No. 07,544,719, filed Jun. 27, 1990, now abandoned which in turn is a continuation in part of application Ser. No. 453,649, filed on Dec. 20, 1989, now abandoned.

This invention is directed to $C^{63}$-amide derivatives of 34-de(acetylglucosaminyl)-34-deoxyteicoplanins of the formula I

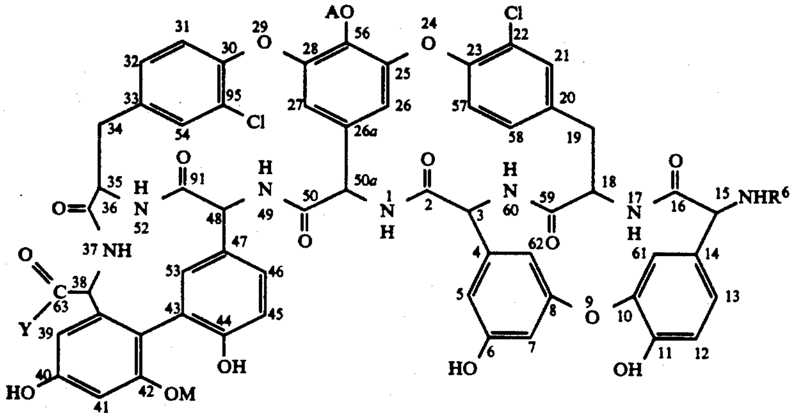

I wherein:

A represents N[($C_9$–$C_{12}$)aliphatic acyl]-beta-D-2-deoxy-2-aminoglucopyranosyl;

$R^6$ is hydrogen or a protecting group of the amine function;

M represents alpha-D-mannopyranosyl;

Y represents a di- or poly-amine group of the formula $$-NR-[(CH_2)_mNR^1]_n-X-[(CH_2)_kNR^2]_h-(CH_2)_p-NR^3R^4$$

wherein:

R is hydrogen or linear or branched ($C_1$–$C_8$)alkyl;

$R^1$ is hydrogen or linear or branched ($C_1$–$C_8$)alkyl;

$R^2$ is hydrogen or linear or branched ($C_1$–$C_8$)alkyl;

$R^3$ and $R^4$ are each independently hydrogen, linear or branched ($C_1$–$C_8$)alkyl optionally bearing a $NH_2$, OH or SH substituent or taken together with the adjacent nitrogen atom, form a 5 to 7 membered saturated heterocyclic ring which may contain a further heteroatom selected from —S—, —O— and —$NR^5$—wherein $R^5$ is hydrogen, ($C_1$–$C_4$)alkyl, phenyl, or phenyl-($C_1$–$C_4$)alkyl m, k and p each independently represent an integer from 2 to 8;

n and h, each independently, represent an integer from 0 to 4;

X represents a single bond, or when n is 1, taken together with the adjacent group $NR^1$, it may represent a bifunctional radical of the formula:

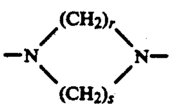

or

-continued

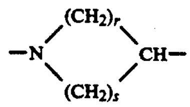

wherein r and s each independently represent an integer from 1 to 6 with the proviso that their sum is an integer from 3 to 8; and their addition salts with acids.

According to a preferred embodiment of this invention, the ($C_9$–$C_{12}$) aliphatic acyl radicals of the symbol A preferably are fully saturated or have one unsaturation. Most preferably, they are the following radicals: (Z)-4-decenoyl, 8-methylnonanoyl, decanoyl, 8-methyldecanoyl, 9-methyldecanoyl, 6-methyloctanoyl, nonanoyl, 10-methylundecanoyl and dodecanoyl.

The symbols R, $R^1$ and $R^2$, preferably represent hydrogen or linear or branched alkyl radicals of 1 to 4 carbon atoms.

The symbols $R^3$ and $R^4$ each independently preferably represents hydrogen, linear or branched alkyl radicals of 1 to 4 carbon atoms optionally bearing a $NH_2$, OH or SH substituent or $R^3$ and $R^4$ taken together with the adjacent nitrogen atom form a 5 to 7 membered saturated heterocyclic ring which may contain a further heteroatom selected from —S—, —O— and —$NR^5$—, the following heterocyclic rings being the most preferred ones: pirrolidine, piperidine, oxazolidine, thiazolidine, isoxazolidine, isothiazolidine, morpholine, piperazine, thiomorpholine, hexahydroazepine, hexahydro-1,5- diazepine and hexahydro-1,4-diazepine; $R^5$ preferably is hydrogen or $C_1$–$C_4$ alkyl.

The symbols m, k and p preferably represent integers from 2 to 6, most preferably, from 2 to 4.

The symbol n and h preferably represents 0, 1 or 2, most preferably 0 or 1.

The symbol X preferably represents a single bond or, when n is 1, taken together with the adjacent group $NR^1$ represents a bifunctional radical of the formula

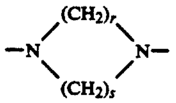

or

-continued

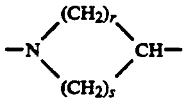

wherein r and s are both 2 or one is 1 and the other is 2 or 3.

According to the general definitions given above representative examples of the group:

$$-NR-[(CH_2)_mNR^1]_n-X-[(CH_2)_kNR^2]_h-(CH_2)_p-NR^3R^4$$

are the following:

$-NH(CH_2)_2NH_2$;
$-NH(CH_2)_3N(CH_3)_2$;
$-NCH_3(CH_2)_3N(CH_3)_2$;
$-NC_2H_5(CH_2)_3N(n-C_4H_9)_2$;
$-NH(CH_2)_3NH(n-C_8H_{17})$:
$-NCH_3(CH_2)_3NHCH_3$;

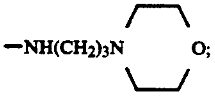 ; 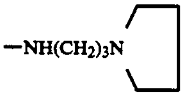 ;

$-NH(CH_2)$hd 3NH$(CH_2)_2OH$;
$-NH(CH_2)_2NH(CH_2)_4SH$;
$-NCH_3(CH_2)_4-NC_2H_5(CH_2)_2NHC_2H_5$;
$-NH(CH_2)_4NH_2$;
$-NCH_3(CH_2)_6N(CH_3)_2$;
$-NC_2H_5(CH_2)_5NH_2$;

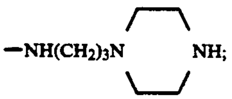

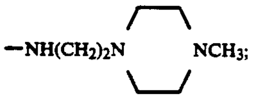

$-NH(CH_2)_2NH(CH_2)_2NH_2$;
$-NH(CH_2)_3NH(CH_2)_3NH_2$;
$-NH(CH_2)_3N[(CH_2)_3NH_2]_2$;
$-NH(CH_2)_3N[(CH_2)_3OH]_2$;
$-NH(CH_2)_3NH(CH_2)_4NH_2$;
$-NH(CH_2)_4NH(CH_2)_3NH_2$;
$-NH(CH_2)_3NH(CH_2)_2NH(CH_2)_3NH_2$;
$-NH(CH_2)_3NH(CH_2)_3NH(CH_2)_3NH_2$;
$-NH(CH_2)_3NH(CH_2)_4NH(CH_2)_3NH_2$;

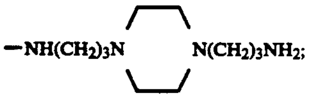

$-NH(CH_2CH_2NH)_2CH_2CH_2NH_2$;
$-NH(CH_2CH_2CH_2NH)_3CH_2CH_2CH_2NH_2$;
$-NCH_3(CH_2)_2NH(CH_2)_3N(CH_3)_2$;
$-NCH_3(CH_2)_3NCH_3(CH_2)_3N(CH_3)_2$;
$-NCH_3(CH_2)_3NH(CH_2)_4N(n-C_4H_9)_2$;
$-NH(CH_2)_3NH(CH_2)_4NH(n-C_8H_{17})$;
$-NH(CH_2)_3NH(CH_2)_4NH(CH_2)_3N(n-C_4H_9)_2$;
$-NH(CH_2)_3NH(CH_2)_4NH(CH_2)_3NH(n-C_8H_{17})$;
$-NCH_3(CH_2)_3NCH_3(CH_2)_3NCH_3(CH_2)_3NHCH_3$;
$-NCH_3(CH_2)_3NCH_3(CH_2)_3NCH_3(CH_2)_3N(n-C_4H_9)_2$;

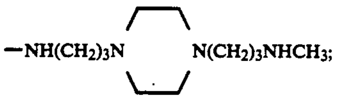

$-NH(CH_2)_3NN(CH_2)_3N(CH_2)_3N(CH_3)_2$;
$-NH(CH_2)_3NN(CH_2)_3NH(n-C_8H_{17})$;
$-NH(CH_2)_3NN(CH_2)_3N(n-C_4H_9)_2$
$-NH(CH_2)_2-NN(CH_2)_2-NHCH_3$

The compounds of this invention show antimicrobial activity, in particular, against gram-positive bacteria, including Group A Streptococci and some coagulase-negative Staphylococci.

Various $C^{63}$-amide derivatives of teicoplanin complex, single components and the aglycone and pseudo aglycones thereof are described in European Patent Application Publication No. 218099 and International Patent Application Publication No. WO 88/06600.

The compounds of this invention are prepared by amidation of the corresponding 34-de(acetylglucosaminyl)-34-deoxy-teicoplanin derivatives of formula I wherein Y is OH, (i.e. the corresponding carboxy acids). These starting materials are specifically described in the European Patent Application Publication No. 290922 or can be prepared according to the procedure disclosed therein.

The above mentioned starting materials are prepared either from the teicoplanin $A_2$ complex (as resulting from fermentation operations) or from its five main components (see: U.S. Pat. No. 4,542,018; A. Borghi et al., J. Antibiot. Vol. 37, 615-620, 1984; C.J. Barna et al. J. Am. Chem. Soc. 1984, 106, 4895-4902) by elimination of the acetylglucosaminyl rest at the position 34.

As it is known in the art, the above mentioned five main components of teicoplanin $A_2$ complex are characterized by the fact that the aliphatic acyl moiety of the beta-D-2-deoxy-2-aminoglucopyranosyl rest is a ($C_{10}$-$C_{11}$) aliphatic aqyl, namely: (Z)-4-decenoyl, 8-methylnonanoyl, decanoyl, 8-methyldecanoyl or 9-methyldecanoyl. Accordingly, the resulting substances used as starting material for the manufacture of the compounds of this invention can be either individual products or mixtures of one or more products. Since said starting materials for the preparation of the compounds of this invention can be used in both said forms, the resulting end products may, in turn, be individual compounds or mixtures of two or more compounds of the above formula I. These mixtures of compounds are also part of the invention and may be used as such for their biological applications and uses or may be eventually separated in their individual components by known procedures described in the art. Examples of separation procedures suitable for the purpose of obtaining individual components from end products mixtures of teicoplanin amide derivatives are those described in the following documents: European Patent Applications Publication No. 218099 and International Patent Application Publication No. WO 88/06600.

Other starting materials for the preparation of the compounds of this invention can be obtained by applying the process of the European Patent Application Publication No. 290922 to teicoplanin compounds such as those described as compound B (identified also as "RS-4" in the papers mentioned below) and compound A (identified also as "RS-3" in the papers mentioned below) in the European Patent Application Publication No. 306645, and those identified as teicoplanin compounds RS-1 and RS-2 in the paper given by M. Zanol et al. at the 17th International Symposium on Chromatography, Vienna, Sep. 25–30, 1988 (see also A. Borghi et al. The Journal of Antibiotics, Vol. 42, No. 3, 361–366, 1989). Said teicoplanin compounds are characterized by the fact that the aliphatic acyl moieties of the beta-D-2-deoxy-2-amino-glucopyranosyl rest are respectively: nonanoyl, 6-methyloctanoyl 10-methylundecanoyl and dodecanoyl.

The compounds RS-3 (compound A) and RS-4 (compound B) can be obtained by fermentation of *Actinoplanes teichomyceticus* strains. In particular, a strain of *Actinoplanes teichomyceticus* which is characterized with our internal code No. A-184 has proved to be a suitable producer of the above mentioned teicoplanin-like derivatives. A sample of said strain has been deposited on Jul. 21, 1987 at the ATCC (American Type Culture Collection, 12301 Parklawn Drive, Rockville, MD 20852 U.S.A.) under the conditions established by the Budapest Treaty on the International Recognition of the Deposit of Microorganisms for the Purposes of Patent Procedure where it has been assigned the following ATCC number 53649.

The above strain identified by the ATCC No. 53649 is an artificial mutant of Actinoplanes teichomyceticus ATCC 31121, obtained by treatment with N-methyl-N-nitro-N-nitrosoguanidine and selected on the basis of its ability to produce substantial amounts of teicoplanin-like antibiotics different from the five major components of the teicoplanin complex.

Mutant A-184 shows substantially the same morphological and physiological characteristics as the parent strain ATCC 31121 described in U.S. Pat. No. 4,239,751.

It has now been found that small amounts of RS-3 and RS-4 may be produced also by the parent strain *Actinoplanes teichomyceticus* ATCC 31121 under proper fermentation conditions, but the isolation of the small quantity of RS3 and RS4 from the much larger amounts of the major components of teicoplanin complex produced by said microorganism is very laborious and is not practical for obtaining the desired compounds in a scale suitable for experimental purposes and practical utilization.

Also mutant A-184 produces a certain amount of the major components of teicoplanin complex together with the RS-3 and RS-4 compounds, but their relative ratio in the fermentation broth is much lower than that resulting from the parent strain. Therefore, the separation and recovery of the RS-3 and RS-4 compounds from the fermentation broth of mutant A-184 is much simpler and substantial amounts of the RS3 and RS4 teicoplanin-like derivatives can be obtained.

For the production of RS-3 and RS-4, the *Actinoplanes teichomyceticus* producing strain is fermented under aerobic conditions in an aqueous nutrient medium containing assimilable sources of carbon, nitrogen and inorganic salts.

Preferred carbon sources are glucose, mannose, galactose, starch, corn mean and the like. Preferred nitrogen sources are ammonia, nitrates, soybean meal, peptone, meat extract, yeast extract, tryptone, aminoacids, and the like. Among the inorganic salts which can be incorporated in the culture media there are the customary soluble salts capable of yielding sodium, potassium, iron, zinc, cobalt, manganese, magnesium, calcium, ammonium, chloride, iodide, carbonate, sulfate, phosphate, nitrate and the like ions.

Ordinarily, the antibiotic-producing strain is pre-cultured in a shake flask, then the culture is used to inoculate jar fermenters for production of substantial quantities of the antiobiotic substances. The medium used for the pre-culture can be the same as that employed for larger fermentations, but other media can also be employed. The producing-strain can be grown at temperatures between 20° C. and 40° C., preferably between 26° C. and 32° C.

During fermentation, the antibiotic production can be monitored by testing broth or mycelial extract samples for antibiotic activity for instance by bioassays or TLC or HPLC procedures.

Sensitive organisms to the antibiotics of this invention such as *Bacillus subtilis* and *S. aureus* can be used as test organisms. The bioassay is conveniently performed by the agar diffusion method on agar plates. Maximum production of antibiotic activity generally occurs between the second and the fifth day after inoculation.

The recovery of the antibiotic substances from the fermentation broths of the producing microorganism is conducted according to known per se techniques which include extraction with solvents, precipitation by adding non-solvents or by changing the pH of the solution, partition chromatography, reverse-phase partition chromatography, ion-exchange chromoatography, affinity chromatography and the like.

A preferred precedure includes an affinity chromatography on immobilized D-Alanyl-D-Alanine followed by reverse-phase column chromatography.

Immobilized D-Alanyl-D-Alanine matrices suitable for the present recovery process are disclosed in Eropean Patent Application Publication No. 122969. The preferred matrix in the present process is D-Alanyl-D-alanine coupled with a controlled pore cross-linked polydextrane.

The fermentation broth can be subjected to the affinity chromatography directly after filtration or after a preliminary purification procedure. This latter procedure includes making the whole fermentation mass basic, preferably between pH 9 and 11.5, in order to solubilize the antibiotic substance adsorbed on the mycelium and then filtering. The clear filtrate is brought to pH between 7 and 8 and then subjected to affinity chromatography on immobilized D-Alanyl-D-Alanine, either in column or batchwise.

Elution is performed at more basic pH values (preferably between 9.0 and 11.0) by means of an aqueous base. This aqueous base may be ammonia, a volatile amine, an alkali or alkali metal hydroxide or a basic buffered solution optionally in the presence of a polar organic solvent such as a polar water-miscible solvent. Fractions are collected, neutralized with an acid (either organic or inorganic, preferably, formic acid) and examined by HPLC to individuate those fractions which contain workable amounts of RS3 and RS4 (the term "workable amount" is intended to mean that the amount of desired compound(s) contained in the eluted solution together with the major components of the teicoplanin complex is sufficient to permit its isolation in an appreciable quantity with the usual separation and purification techniques). Usually, the eluted fractions which contain at least 2% of one of the desired compounds on the total HPLC area relative to teicoplanin and teicoplanin-like products, are considerd to contain a "workable amount" of the desired compound). Under the following analytical HPLC conditions: Apparatus: Hewlett Packard liquid chromatograph, mod. 1084 B; the UV detector is set at 254 nm. Column: Erbasil C18 5 micrometer, 150×4.6 mm (Carlo Erba) Mobile phase: A: 0.02M $NaH_2PO_4/CH_3CN$ (95:5) B: 0.02M $NaH_2PO_4/CH_3CN$ (25:75)

| Gradient | |
|---|---|
| min | % B |
| 0 | 8 |
| 40 | 40 |
| 45 | 55 |
| 48 | 8 |
| 50 | stop |

Flow rate: 1.5 ml/min

Column pressure: 200 atm

Injection volume: 20 microliter

Attenuation: 8

Chart speed: 0.5 cm/min

Standard: teicoplanin A2 complex (A. Borghi et al.: The Journal of Antibiotics, Vol. 37, No. 6, pp 615-620, June 1984) dissolved in water to give a solution at the concentration of 1156.5 microgram/ml, the compound wherein the aliphatic acyl group of the beta-D-2-deoxy-2-aminoglucopyranosyl moiety is 6-methyloctanoyl (compound A) has a retention time (RT) value of 19.93 minutes while the compound wherein the aliphatic acyl group of the beta-D-2-deoxy-2-aminoglucopyranosyl moiety is n-nonanoyl (compoung B) has an RT value of 20.96 minutes. As a reference, the RT value for TA2-2, under the same operational conditions is 24.71 minutes.

Those fractions which contain workable amounts of the desired compounds (RS3 and RS4) are pooled and concentrated by ultrafiltration and then lyophilized.

The crude product from lyophilization is dissolved in a polar aprotic organic solvent and then submitted in several portions to semi-preparative HPLC using a gradient mixture of a polar aprotic organic solvent and an aqueous ammonium salt as the mobile phase.

Examples of the polar aprotic organic solvent are $(C_1-C_4)$ alkyl, lower alkyl amides or thio-amides, such as preferably dimethylformamide or diethylformamide.

Examples of ammonia salts are ammonia formate, ammonia acetate, methylammonium formate; ammonia formate being preferred.

In this case, the stationary phase is preferably a silanized silica gel, i.e. a silica gel functionalized with $(C_8-C_{22})$alkyl groups.

A preferred mobile phase is represented by mixtures of 0.02M ammonium formate/acetonitrile 95:5 and 0.02M ammonium formate/acetonitrile 25:75.

From the eluates of each portion submitted to preparative HPLC the fractions containing Compound A and B respectively as the major products (HPLC analysis) are isolated and combined with those of the other portions. For instance, in a typical operation two solutions are obtained, the first of which contains about 80 percent of the 6-methyloctanoyl derivative with minor amounts (about 1.5 percent) of the n-nonanoyl compound while the second one contains about 90 percent of the n-nonanoyl compound with about 6 percent of 6-methyloctanoyl compound.

The two solutions are concentrated under vacuum, ultrafiltered and then lyophilized giving two solid products that are further purified by repeating the semi-preparative HPLC to yield pure RS-3 and RS-4.

Raw extracts, rich in RS-1 and RS-2 were obtained from the mother liquors of the preparation of several batches of teicoplanin obtained under submerged aerobic fermentation conditions from *Actinoplanes teichomyceticus* ATCC 31121. About 500 mg of crude extract were charged in each run on the Jobin Yvon chromatograph, equipped with a column (50 cm, 2 cm I.D.), packed with RP-18 7 um (Merck) and eluted with a mixture of 0.02M monobasic sodium phosphate/acetonitrile 73/27. After evaporation under vacuum of the acetonitrile, the extract was passed through a column of RP-8 and eluted first with water, to eliminate the salt, and then with water/acetonitrile 30/70. A partially purified mixture was thus obtained. RS-1 and RS-2 present in this last mixture were then isolated by preparative HPLC, using the chromatograph mod. 1084 equipped with a RP-18 7 um column (Merck, 25 cm, 1 cm I.D.) and the same phosphate/acetonitrile eluent used in the first step. After a second desalification step, carried out as described above, and the elimination of acetonitrile, the aqueous fractions containing RS-1 and RS-2 were lyophilized.

The amidation procedures described in the two above mentioned European Patent Application Publication No. 218099 and International Patent Application Publication No. WO 88/06600 can be used also for the preparation of the compounds of this invention. Said procedures involve condensing the carboxy acid starting materials mentioned above with an excess of the appropriate amine of the formula II:

$$NHR-[(CH_2)_mNR^1]_n-X-[(CH_2)_kNR^2]_h-(CH_2)_p-NR^3R^4$$

wherein R, $R^1$, $R^2$, $R^3$, $R^4$, X, m, n, h, k and p have the same meanings as above, in an inert organic solvent in the presence of a condensing agent selected from $(C_1-C_4)$alkyl, phenyl or heterocyclyl phosphorazidates at a temperature between 0° C. and 20° C. If the amine reactant contains other functions which are not inert under the selected reaction conditions, said functions are suitably protected by means of per se known protecting groups.

According to a preferred embodiment of this invention, the compounds of formula I wherein Y is a di-or poly-amine group as defined above are prepared by reacting an "activated ester", of the carboxylic acid of the same formula I, wherein Y is OH and the $N^{15}$-amino function is preferably protected, with the appropriate amine II.

The $N^{15}$-amino function can be protected by methods known per se in the art such as those described in reference books like T.W. Greene, "Protective Groups in Organic Synthesis", John Wiley and Sons, New York, 1981, and M. Mc. Omie "Protecting Groups in Organic Chemistry" Plenum Press, New York, 1973. These protecting groups must be stable at the conditions of the reaction process, must not unfavorably interfere with the amidation reaction, and must be easily cleavable and removable from the reaction medium at the end of the reaction without altering the newly formed amide bond.

Representative examples of N-protecting groups which may be advantageously used in the process of the invention for protecting the $N^{15}$ primary amino function of the teicoplanin starting material and, when appropriate, the $NR^3R^4$ moiety of the amine II reactant, are carbamate forming reagents characterized by the following oxycarbonyl groups: 1,1-dimethylpropynyloxycarbonyl, t-butyloxycarbonyl, vinyloxycarbonyl, aryloxycarbonyl, cinnamyloxycarbonyl, benzyloxycarbonyl, p-nitrobenzyloxycarbonyl, 3,4-dimethoxy-6-nitrobenzyloxycarbonyl, 2,4-dichlorobenzyloxycarbonyl, 5-benzisoxazolylmethyloxycarbonyl, 9-anthranylmethyloxy-carbonyl, diphenylmethyloxycarbonyl, isonicotinyloxycarbonyl, diphenylmethyloxycarbonyl, isonicotinyl-oxycarbonyl, S-benzyloxycarbonyl, 2,2,2-trichloro-ethoxycarbonyl, 2,2,2-trichloro-t-butoxycarbonyl, and the like. Other suitable N-protecting agents are aldehydes or ketones, or derivatives thereof which are capable of forming Schiff bases with the amino group to be protected.

Preferred examples of such, Schiff base forming agents are benzaldehydes and particularly preferred is 2-hydroxybenzaldehyde (salicylaldehyde). A convenient means of protection in the case the amine II reactant has R different from hydrogen and contains a primary amino function (e.g. $R^3$ and $R^4$ both represent hydrogen) is, in some instances, the formation of a benzyliden derivative which may be prepared by reacting the amine with benzaldehyde in a lower alkanol, such as ethanol, preferably at room temperature. After the reaction with the selected teicoplanin starting material has been completed, the benzylidene protecting group may be removed as known in the art, e.g. by catalytic hydrogenation, using, for instance, Palladium on carbon as the catalyst.

However, in all cases where catalytic hydrogenation is applied, attention should be paid to the presence of groups which may be modified by catalytic hydrogenation. A typical consequence of the catalytic hydrogenation of an amino-protected derivative of formula I wherein A represents a group as above defined whose acyl portion is (Z)-4-decenoyl (or a mixture containing it) is that, at least partially, the decenoyl compound is transformed into the corresponding decanoyl compound. Therefore, when the removal of the protecting group is carried out through catalytic hydrogenation and the 34-de(acetylglucosaminyl)-34-deoxy-teicoplanin starting material is (or contains) a derivative of component 1 of teicoplanin $A_2$ complex (whose acyl portion is (Z)-4-decenoyl) the final amide product, in most cases, does not contain the corresponding derivative but, rather, a proportionally larger amount of the derivative of the component 3 whose acyl rest is decanoyl.

If a final compound containing the amide derivative of teicoplanin $A_2$ complex component 1 is desired, the N-protecting group must be selected among those which can be removed under conditions which do not imply hydrogenation of the acyl portion or hydrolysis of the sugar moieties of the teicoplanin substrate. For example, an N-protecting group which is removable under mild conditions is selected from beta-halo-alkoxycarbonyl groups, such as 2,2,2-trichloro-tert-butoxycarbonyl, which can be removed according to the procedures described by H. Eckert et al., in Angew, Chem. Int. Ed. Engl. 17, No.5, 361-362 (1978).

As it is appreciated by the skilled technician, the ultimate choice of the specific protecting group depends on the characteristics of the particular amide derivative which is desired. In fact, this amide function of the final compound should be stable at the condition of removal of the protecting group(s).

Since the conditions of removal of the different protecting groups are known, the skilled technician is capable of selecting the proper protecting group.

In some cases, when the amine II contains two primary amino groups (e.g. R, $R^3$ and $R^4$ all representing hydrogen) it may be convenient to obtain a mixture of two reaction products resulting from the formation of the amidic bond with each of the two primary aminic functions and to separate them by common procedures such as flash column chromathography, reverse-phase column chromathography or preparative HPLC.

The formation of "activated esters" is described in general terms in Fieser and Fieser, "Reagent for Organic Synthesis", John Wiley and Sons Inc. 1967pages 129-130.

Examples of said activated ester forming reagents that can be conveniently used in the process of the invention are those described by R. Schwyzer et al. in Helv. Chim. Acta, 1955, 38, 69-70 and encompass:

$ClCH_2CN$, $BrCH_2COOC_2H_5$, $BrCH(COOC_2H_5)_2$, $ClCH_2COCH_3$, $ClCH_2$— 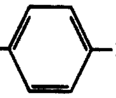 —$NO_2$, $ClCH_2CH_2N(C_2H_5)_2$ A preferred reagent of this type is chloroacetonitrile. In this case, chloroacetonitrile itself or dimethylformamide (DMF) can be used as preferred solvents.

Generally, inert organic solvents useful for the formation of "activated esters" are those organic aprotic solvents which do not unfavorably interfere with the reaction course and are capable of, at least partially, solubilizing the carboxyacid starting material.

Examples of said inert organic solvents are organic amides, alkyl ethers, ethers of glycols and polyols, phosphoramides, sulfoxides and aromatic compounds. Preferred examples of inert organic solvents are: dimethylformamide, dimethoxyethane, hexamethylphosphoramide, dimethylsulfoxide, benzene, toluene and mixtures thereof.

More preferably, the solvent is selected from acetonitrile, dimethylsulfoxyde, dimethylformamide. The formation of the activated ester is generally conducted in the presence of a base which does not interfere with the reaction course such as a trialkylamine like triethylamine, sodium or potassium carbonate or bicarbonate. Generally, the base is employed in a 2 to 6 molar proportion to the teicoplanin carboxy acid starting material and, preferably, it is used in an about three-fold molar excess. A preferred base is triethylamine.

The "activated ester" forming reagent is used in a large excess over the teicoplanin carboxy acid starting material. It is in general used in a 5 to 35 molar proportion and, preferably, it is used in an about 20 to 30 times molar excess. The reaction temperature is between 10° C. and 60° C. and preferably between 15° C. and 30° C. As usual, the reaction time depends on the other specific reaction parameters and may be generally between 3 and 48 hours.

In this case, the reaction course may be followed by HPLC or TLC to determine when the reaction may be considered as completed and the procedures to recover the desired intermediate can be started. The "activated ester" intermediate can be directly used in the same reaction medium where it is prepared, however, in general, it is isolated by precipitation with non-solvents or by extraction with solvents and it is used as such, without further purification, in the next reaction step. If desired, however, it may be purified by column chromatography such as flash column chromatography or reverse-phase column chromatography.

The obtained "activated ester" intermediate is then reacted with a molar excess of the amine derivative of formula II $$NHR-[(CH_2)_mNR^1]_n-X-[(CH_2)_kNR^2]_h-(CH_2)_p-NR^3R^4$$

in the presence of an organic polar solvent at a temperature between 5° C. and 60° C., preferably between 10° C. and 30° C.

The organic polar solvent can be in this case a polar protic or aprotic solvent.

Preferred examples of organic polar protic solvents are lower($C_2$–$C_4$) alkanols such as, ethanol, n-propanol, iso-propanol, n-butanol and the like, or mixtures thereof, preferably used in the dry form.

Preferred examples of organic polar aprotic solvent are N,N-dimethylformamide (DMF), hexamethylphosphoramide (HMPA), or mixtures thereof, 1,3-dimethyl-3,4,5,6-tetrahydro-2(1H)pyrimidone (DMPU), dimethylsulfoxyde or dimethoxyethane.

The reaction of the "activated ester" with the selected amine can be carried out at a temperature between 5° C. and 60° C. but the preferred temperature is generally comprised between 10° C. and 30° C., most preferably between 20° C. and 25° C., while a preferred molar proportion between the "activated ester" intermediate and the amine II as above defined is from 1:5 to 1:30, and more preferably from 1:10 to 1:20. The reaction course may be monitored as usual by TLC or HPLC.

The amide derivative obtained from the amidation reaction is recovered from the reaction solution according to common procedures, for instance, by evaporation of the solvent or by addition of a non-solvent. The removal of the amino-protecting group is usually carried out on the crude product isolated from the amidation reaction Examples of procedures for the removal of said protecting groups from teicoplanin derivatives are described for instance in International Application Publication No. WO 88/06600.

If catalytic hydrogenation procedures are used, the reaction is usually carried out in the presence of a diluted aqueous strong acid, preferably a mineral acid, in an organic solvent miscible with said diluted aqueous strong acid. The filtrate from the reaction is then worked for the recovery of either the mineral acid addition salt of the amide of formula I or the corresponding free base. Analogous procedures are followed when the amino-protecting group is a group which can be removed by treating with diluted mineral acids (e.g. Schiff base or a $C_1$–$C_4$ alkoxy carbonyl group) under conditions which do not cause the splitting of the sugar moieties (e.g. low temperatures, short reaction time).

For the isolation of the acid addition salt, the reaction solution resulting from the splitting of the amino-protecting group is generally brought to a pH value between 6 and 7 by addition of an aqueous base, e.g. aqueous sodium hydroxyde, and, after evaporation of the solvent under reduced pressure, the resulting solid is separated in the form of an addition salt with the strong acid which has been added during the de-protection step. Such product may be further purified by common techniques e.g. column chromatography, precipitation from solutions by addition of non-solvents, preparative HPLC and similar. The acid addition salt may be converted to the corresponding free base of formula I by suspending or dissolving the acid addition salt in an aqueous solvent which is then brought to an appropriate pH value whereby the free-base form is restored. The product is then recovered, for instance, by extraction with an organic solvent or is transformed into another acid addition salt by adding the selected acid and working up as above.

Sometimes, after the above operation, it may be necessary to submit the recovered product to a common desalting procedure.

For example, column chromatography on controlled pore polydextrane resins (such as SEPHADEX L H 20) or silanized silica gel may be conveniently used. After eluting the undesired salts with an aqueous solution, the desired product is eluted by means of linear gradient or step-gradient of a mixture of water and a polar or apolar organic solvent, such as acetonitrile/water or acetonitrile/aqueous acetic acid from 5% to about 100% acetonitrile and then recovered by evaporation of the solvent or by lyophilization.

When a compound of formula I is obtained in the free-base form, it can be transformed into the corresponding acid addition salt by suspending or dissolving the free base form in an aqueous solvent and adding a slight molar excess of the selected acid. The resulting solution or suspension is then lyophilized to recover the desired acid addition salt. Instead of lyophilizing, in some instances, it is possible to recover the final salt through precipitation by addition of a non-solvent mixable with water.

In case the final salt is unsoluble in an organic solvent where the free base form is soluble it may be recovered by filtration from the organic solution of the non-salt form after addition of the stoichiometric amount or a slight molar excess of the selected acid.

Representative and suitable acid addition salts of the compounds of formula I include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, camphoric, glutaric, glycolic, phthalic, tartaric, lauric, stearic, salicylic, methanesulfonic, benzenesulfonic, sorbic, picric, benzoic, cinnamic and the like acids.

Preferred addition salts of the compounds of this invention are the pharmaceutically acceptable acid addition salts.

With the term "pharmaceutically acceptable acid addition salts" are intended those salts with acids which from biological, manufacturing and formulation standpoint are compatible with the pharmaceutical practice.

Example of acids suitable for the "pharmaceuticaly acid addition salts" includes those listed above.

A characteristic of the compounds of this invention which further differentiate them from the corresponding starting compound is the configuration of the amidic bond at the 51, 52 position which is "cis", while the configuration of the same bond in the starting teicoplanin carboxylic acid is "trans". This implies that the conformation of the teicoplanin core of the new compounds is remarkably modified with respect to that of the corresponding starting materials.

The compounds of the present invention in the form of both the free bases and their acid addition salts are useful as antibacterial agents, mainly active against gram-positive bacteria. More particularly, they are useful in the treatment of infections caused by Group A Streptococci (e.g. *Streptococcus pyogenes*). In fact, at present, they are the most active derivatives among teicoplanin antibiotics against the microorganisms of this genus. They are also more active than teicoplanin against coagulase-negative Staphylococci (e.g. *Staphylococcus epidermidis* and *Staphylococcus haemolyticus*), in particular, *Staphylococcus haemolyticus*.

The antibacterial activity, of the compounds of the invention is determined in vitro by means of standard agar-dilution tests in microtiter. ISOSENSITEST broth (Oxoid) and TODD-HEWITT broth (Difco) are used for growing Staphylococci and Streptococci. respectively. Broth cultures are diluted so that the final inoculum is about $10^4$ forming units/ml (CFU/ml). Minimal inhibitory concentration (MIC) is considered as the lowest concentration which shows no visible growth after 18-24 h incubation at 37° C.

The results of the antibacterial testing of representative compounds of formula I are summarized in Table I.

TABLE I

In vitro (MIC microgram/ml)

| Test Organisms | Compounds No. 1 | 2 | 3 | 4 | 5 |
|---|---|---|---|---|---|
| *Staphylococcus aureus* TOUR | 4 | 2 | 2 | 2 | 2 |
| *Staphylococcus epidermidis* ATCC 12228 | 0.25 | 0.12 | 0.12 | 0.12 | 0.12 |
| *Staphylococcus haemolyticus* L 602 | 2 | 2 | 0.5 | 0.5 | 1 |
| *Streptococcus pyogenes* C 203 | 0.12 | 0.06 | 0.016 | 0.016 | 0.032 |
| *Streptococcus pneumoniae* UC 41 | 0.5 | 0.25 | 0.25 | 0.25 | 1 |
| *Streptococcus faecalis* ATCC 7080 | 2 | 2 | 2 | 2 | 4 |

| Test Organisms | Compounds No. 6 | 7 | 12 | 14 | 32 | 33 |
|---|---|---|---|---|---|---|
| *Staphylococcus aureus* TOUR | 2 | 1 | 1 | 2 | 0.12 | 0.12 |
| *Staphylococcus epidermidis* ATCC 12228 | 0.12 | 0.06 | 0.12 | 0.12 | 0.004 | 0.004 |
| *Staphylococcus haemolyticus* L 602 | 1 | 1 | 1 | 0.5 | 0.032 | 0.032 |
| *Streptococcus pyogenes* C 203 | 0.06 | 0.032 | 0.06 | 0.016 | 0.008 | 0.004 |
| *Streptococcus pneumoniae* UC 41 | 0.25 | 0.25 | 0.25 | 0.5 | 0.12 | 0.12 |
| *Streptococcus faecalis* ATCC 7080 | 2 | 2 | 2 | 2 | 0.12 | 0.12 |

The activity of the compounds of this invention against *Streptococcus pyogenes* is, in some cases, higher than that of teicoplanin and the most active compounds of European Patent Application Publication No. 290922, European Patent Application Publication No. 218099 and Internation Patent Application Publication No. WO 88/06600 whose MIC (microgram/ml) against the same microorganism is never lower than 0.06.

For the most useful applications of the biological activity of the compounds of this invention, is of particular interest their selectivity against *Streptococcus pyogenes* which is indicated by the comparison of the MIC values against said microorganism with the MIC values against the other test organisms reported in Table I above, in particular, *Staphylococcus aureus*.

The activity against several clinical isolates of *Streptococcus pyogenes* of compounds 3, 5 and 32 is shown in Table II.

TABLE II

| *S. pyogenes* strain No. | MIC (microgram/ml) Compound 3 | Compound 5 | Compound 32 | Teicoplanin |
|---|---|---|---|---|
| L-33 | 0.063 | 0.032 | 0.004 | 0.063 |
| L-317 | 0.008 | 0.016 | 0.008 | 0.063 |
| L-800 | 0.032 | 0.063 | 0.008 | 0.063 |
| L-801 | 0.032 | 0.004 | 0.004 | 0.063 |
| L-802 | 0.032 | 0.063 | 0.016 | 0.063 |
| L-803 | 0.063 | 0.032 | 0.008 | 0.063 |
| L-804 | 0.032 | 0.032 | 0.008 | 0.063 |
| L-805 | 0.032 | 0.063 | 0.004 | 0.063 |
| L-1303 | 0.063 | 0.063 | 0.004 | 0.063 |
| L-1304 | 0.032 | 0.063 | 0.004 | 0.125 |
| L-1306 | 0.125 | 0.063 | 0.004 | 0.125 |
| L-1315 | 0.063 | 0.125 | 0.008 | 0.063 |
| L-1316 | 0.063 | 0.063 | 0.004 | 0.063 |
| L-1318 | 0.063 | 0.063 | 0.008 | 0.063 |
| L-1319 | 0.063 | 0.125 | 0.008 | 0.063 |

The compounds of this invention show considerably lower activity against bacteria other than Streptococci of Group A and coagulase negative Staphylococci and therefore they can be regarded as antibiotics showing a very narrow and selective spectrum of activity particularly useful for the specific target of combatting Streptococcal infections, with lower probability to select resistant strains of the other genera.

Streptococcal infections are usually responsible for severe pathological complications such as rheumatic fever, nephritis, endocarditis, erysipelas and the like.

The production of antibiotics with very narrow specific spectra is considered as an important need for the development of chemotherapy. See W. Brumfitt et al. in Postgraduate Medical Journal, Vol. 64 (1988) No. 753 pag. 552-558.

A further peculiarity of these compounds which constitutes a further object of the present invention is their ability to inhibit the growth of bacteria resistant to glycopeptide antibiotics of the vancomycin-ristocetin class including teicoplanin.

As can be seen in Table IIa the compounds of the present invention show a surprisingly improved activity in comparison with teicoplanin, vancomycin and the corresponding amides of teicoplanin against glycopeptide resistant Enterococci strains.

In particular, the activity of the compounds of the invention was confirmed through in vitro experiments carried out with clinical isolates resistant to glycopeptide antibiotics such as with *Enterococci faecalis, Enterococci faecium*, as shown in Table IIa.

Therefore, a further aspect of the invention concerns the use of the present compounds for the treatment of infectious diseases provoked by bacteria which are resistant to glycopeptide antibiotics of the vancomycin and ristocetin type such as teicoplanin and its amide derivatives, in particular by Enterococci strains resistant to glycopeptide antibiotics.

The amide derivatives of teicoplanin which are reported in Table IIa were described in EP-A 218099, EP-A 326873, International Patent Application Serial No. PCT/EP90/00400 and in European Patent Application Serial No. 89120267.

TABLE IIa

In vitro activity (MIC, mcg/ml) of $C^{63}$-amide derivatives of 34-de(acetylglucosaminyl)-34-deoxy teicoplanin CTI-AMIDES, in comparison with the corresponding teicoplanin amides, teicoplanin (TEICO) and vancomycin (VANCO), against glycopeptide-resistant Enterococci (E.)

| ORGANISM | STRAIN NO. (internal code) | COMPOUNDS OF THE INVENTION | | | | | TECOPLANIN AMIDES | | | | | TEICO | VANCO |
|---|---|---|---|---|---|---|---|---|---|---|---|---|---|
| | | 1 | 2 | 3 | 4 | 5 | 1' | 2' | 3' | 4' | 5' | | |
| *E. faecalis* | NCTC 12201 | 32 | 16 | 8 | 32 | 8 | 128 | 128 | 32 | 8 | 32 | 128 | >128 |
| *E. faecalis* | L 560 | 16 | 16 | 16 | 32 | 16 | 128 | 128 | 64 | 64 | 128 | >128 | >128 |
| *E. faecalis* | NCTC 12202 | 32 | 32 | 32 | 64 | 16 | >128 | >128 | 128 | 128 | 64 | 128 | >128 |
| *E. faecium* | NCTC 12203 | 16 | 16 | 8 | 16 | 8 | 128 | 128 | 64 | 32 | 32 | 64 | >128 |
| *E. faecium* | NTCT 12204 | 16 | 16 | 16 | 16 | 8 | >128 | 128 | 64 | 32 | 16 | 64 | >128 |
| *E. faecium* | L 1666 | >128 | >128 | 128 | 128 | 64 | >128 | >128 | >128 | >128 | >128 | >128 | >128 |

The antibacterial activity is determined in vitro by means of standard agar-dilution tests in microtiter. ISOSENSITEST broth (Oxoid) is used for growing Enterococci. Broth cultures are diluted so that the final inoculum is about $5 \times 10^5$ forming units/ml (CFU/ml).

In view of the above reported antimicrobial activity, the compounds of the present invention can be employed as the active ingredient of antimicrobial preparations used in human and veterinary medicine for the prevention and treatment of infections diseases caused by pathogenic bacteria which are susceptible to said active ingredients.

In such treatments, these compounds may be employed as such or in the form of mixtures in any proportion.

The compounds of the present invention can be administered orally, topically or parenterally wherein however, the parenteral administration is preferred. Depending on the route of administration, these compounds can be formulated into various dosage forms. Preparations for oral administration may be in the form of capsules, tablets, liquid solutions or suspensions. As known in the art the capsules and tablets may contain in addition to the active ingredient, conventional excipients such as diluents, e.g. lactose, calcium phosphate, sorbitol and the like, lubricants, e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations generally in the form of aqueous or oily solutions or suspensions, may contain conventional additives such as suspending agents. For topical use the compounds of the present invention may also be prepared in suitable forms to be applied to the skin, the mucous membranes of the nose and throat or bronchial tissues and may conveniently take the form of creams, ointments, liquid sprays or inhalants, lozenges, or throat paints.

For medication of the eyes or ears, the preparation may be presented in liquid or semi-liquid form formulated in hydrophobic or hydrophilic bases as ointments, creams, lotions, paints, or powders.

For rectal administration the compounds of the invention are administered in the form of suppositories admixed with conventional vehicles, such as, for example, cocoa butter, wax, spermaceti or polyethylenglycols and their derivatives.

Compositions for injection may take such forms as suspensions, solutions, or emulsions in oily or aqueous vehicles, and may contain formulatory agents such as suspending, stabilizing and/or dispersing agents.

Alternatively, the active ingredient may be in powder form for reconstitution at the time of delivery with a suitable vehicle, such as sterile water.

The amount of active principle to be administered depends on various factors such as the size and conditions of the subject to be treated, the route and frequency of administration, and the causative agent involved.

The compounds of the invention are generally effective at a dosage comprised between about 0.3 and about 30 mg of active ingredient per kg of body weight, preferably divided in 2 to 4 administrations per day. Particularly desirable compositions are those prepared in the form of dosage units containing from about 20 to about 600 mg per unit.

EXAMPLES

General Procedures

In the following examples the starting material may be the 34-de(acetylglucosaminyl)-34-deoxy teicoplanin $A_2$ complex (i.e. a mixture of compounds obtained from teicoplanin $A_2$ complex according to the procedure of European Patent Application Publication No. 290922, a single component thereof or any mixture of two or more of said components).

The typical complex mixture essentially consists of five components corresponding to formula I above wherein the aliphatic acyl moieties of the beta-D-2-deoxy-2-aminoglycopyranosyl radical represented by the symbol A are respectively: (Z)-4-decenoyl ($AC_1$), 8-methylnonanoyl ($AC_2$), decanoyl ($AC_3$), 8-methyldecanoyl ($AC_4$) and 9-methyldecanoyl ($AC_5$), B is hydrogen, M is alpha-D-mannopyranosyl and Y is OH. This mixture is identified by the acronym $TGAC_{1-5}$. When one of the single components of said mixture is employed as the starting material it is identified as follows: $TGAC_1$, $TGAC_2$, $TGAC_3$, $TGAC_4$ or $TGAC_5$, depending on the specific aliphatic acyl rest of the above mentioned aminoglucopyranosyl radical.

When a mixture of one or more components is used it is indicated according to the same system as for the complex. For instance, the acronym $TGAC_{2-5}$ indicates the mixture of the components 2 to 5 wherein component 1 is no longer present. This mixture is currently obtained from teicoplanin $A_2$ complex according to the procedure of European Patent Application Publication No. 290922 when catalytic hydrogenation is applied which saturates the double bond of component 1 transforming it into component 3. The acronym $TGAC_{2,3}$ indicates a mixture of the components 2, 3 and the acronym $TGAC_{4,5}$ indicates a mixture of the components 4 and 5.

The resulting end products in the following table III are identified by reference to formula I above with the indication for the symbol A of the particular aliphatic acyl substituent of the beta-D-2-deoxy-2-aminoglucopyranosyl radical (A/AC) by using the conventional terms $AC_1$, $AC_2$, $AC_3$, $AC_4$, $AC_5$ as explained above. When a mixture of two or more components is obtained, this is shown through the same formal description as above.

HPLC Analysis is carried out with a VARIAN mod. 5000 LC pump equipped with a 20 microliter loop injector RHEODYNE mod. 7125 and a UV detector at 254 nm.

Columns: pre-column (1.9 cm.) HIBAR LICHRO CART 25-4 (Merck) pre-packed with LICHROSORB RP-8 (20-30 micrometer) followed by a column HIBAR RT 250-4 (Merck) pre-packed with LICHROSORB RP-8 (10 micrometer). Eluents: A, 0.2% aq. $HCOONH_4$; B, $CH_3CN$. Flow rate: 2 mL/min. Injection: 20 microliter. Elution: linear gradient from 20 to 60% of B in A in 30 min. The retention times of some representative compounds are reported in TABLE IIIb.

Acid-Base Titrations. The products are dissolved in MCS (methylcellosolve):$H_2O$ 4:1 (v/v), then an excess of 0.01M HCl in the same solvent mixture is added and the resulting solutions are titrated with 0.01N NaOH. Equivalent weight of some representative compounds are reported in TABLE IIIa.

$^1H$-NMR spectra at 500 MHZ are recorded in the temperature range from 20° C. to 30° C. on a BRUKER AM 500 spectrometra in DMSO-$D_6$ with tetramethylsilane (TMS) as the internal reference (delta=0.00 ppm). Table IIIc reports the most significant chemical shifts (delta, ppm) of some representative compounds.

Method of Preparation a) A solution of 4 g (about 2.5 mmol) of a TGAC (the complex, a single component thereof, or a mixture of two or more of the single components) and 0.36 mL (about 2.6 mmol) of triethylamine (TEA) in 20 mL of DMF is stirred at room temperature for 30 min., while adding 0.4 mL (about 2.8 mmol) of benzyl chloroformate. Then, additional 0.4 mL (about 3.3 mmol) of TEA and 4 mL (about 65 mmol) of chloroacetonitrile are added and stirring is continued at room temperature for 20 h. The reaction mixture is poured into 300 mL of ethyl acetate, the precipitated solid is collected by filtration, and washed with 100 mL of ethyl ether, yielding (after drying in vacuo at room temperature overnight) 4.3 g of crude cyanomethyl ester of $N^{15}$-carbobenzyloxy TGAC.

b) To a stirred solution of the above product in 30 mL of DMF, 35 mmol of the proper reactant amine is added, and the resulting solution is stirred at room temperature overnight. Then, 25 mL of absolute ethanol is added, followed by 250 mL of ethyl acetate. The precipitated solid is collected by filtration, washed with 100 mL of ethyl ether, and dried in vacuo at room temperature for 4 hours, yielding 4.1 g of crude $N^{15}$-carbobenzyloxy compound of formula I, which c) is dissolved in 350 mL of a mixture methanol:0.01N HCl 7:3 (v/v). The resulting solution is adjusted at pH 3.0 with 1N HCl and hydrogenated at 1 atm and room temperature, in the presence of 4 g of 5% Pd/C, while absorbing 120 mL of hydrogen gas within 2 hours. The catalyst is filtered off and the clear filtrate is adjusted at pH 6.5 with 1N NaOH. After adding 300 mL of n-butanol and 15 g of silanized SILICA-GEL (0.06–0.2 mm, Merck), solvents are evaporated at 40° C. under reduced pressure. The solid residue is suspended in 200 mL of water and the resulting suspension is loaded at the top of a column of 400 g of the same silanized SILICA-GEL in water. The column is developed with a linear gradient from 10% to 80% of acetonitrile in 0.1N acetic acid in 20 hours at the flow rate of about 250 mL/h, while collecting 25 mL fractions, which are checked by HPLC. Those fractions containing pure compounds of the title are pooled, and the resulting solution is adjusted at pH 8.5 with 1N NaOH, and then it is concentrated at 40° C. under reduced pressure to a small volume (about 50 mL). The solid which separates is collected by centrifugation, washed with 10 mL of water, then with 250 mL of ethyl ether. After drying at room temperature in vacuo overnight, the compound of the formula I is obtained, as the free base.

For the manufacture of the invention compounds where the $AC_1$ moiety is still present, the step a) is modified by reacting the $TGAC_{1-5}$ complex or the $TGAC_1$, or a mixture of two or more components containing it, with 2,2,2-trichloro-t-butoxy-chloroformate according to the same procedure as above and the first portion of step c) is replaced by contacting the resulting $C^{63}$-amide $N^{15}$-protected amine with zinc in acetic acid according to the procedure described by H. Eckert et al. in Angew. Chem. Int. Ed. Engl. 17, No.5, 361–362 (1978). The purification is carried out in the same way as described in the second part of step c).

By using the appropriate reagents TGAC and a amine of formula:

$$NHR—[(CH_2)_mNR^1]_n—X—[(CH_2)_kNR^2]_h—(CH_2)_p—NR^3R^4$$

under the conditions described above, the compounds represented in Table III are obtained.

TABLE III

| Comp. | Reagents | | End product of formula I | | | |
|---|---|---|---|---|---|---|
| No. | TGAC | Amine | A/AC(*) | B | M(**) | Y |
| 1 | $TGAC_{2-5}$ | $NH_2(CH_2)_3N(CH_3)_2$ | $AC_{2-5}$ | —H | —M | $—NH(CH_2)_3N(CH_3)_2$ |
| 2 | $TGAC_{2-5}$ | $NH_2(CH_2)_3NH(CH_2)_2OH$ | $AC_{2-5}$ | —H | —M | $—NH(CH_2)_3NH(CH_2)_2OH$ |
| 3 | $TGAC_{2-5}$ | $NH_2(CH_2)_3NH(CH_2)_4NH_2$ | $AC_{2-5}$ | —H | —M | $—NH(CH_2)_3NH(CH_2)_4NH_2$(1) |
| 4 | $TGAC_{2-5}$ | $NH_2(CH_2)_3NH(CH_2)_4NH_2$ | $AC_{2-5}$ | —H | —M | $—NH(CH_2)_4NH(CH_2)_3NH_2$(2) |
| 5 | $TGAC_{2-5}$ | $NH_2(CH_2)_3NH(CH_2)_4NH(CH_2)_3NH_2$ | $AC_{2-5}$ | —H | —M | $—NH(CH_2)_3NH(CH_2)_4NH(CH_2)_3NH_2$ |
| 6 | $TGAC_2$ | $NH_2(CH_2)_3N(CH_3)_2$ | $AC_2$ | —H | —M | $—NH(CH_2)_3N(CH_3)_2$ |
| 7 | $TGAC_2$ | $NH_2(CH_2)_3NH(CH_2)_2OH$ | $AC_2$ | —H | —M | $—NH(CH_2)_3NH(CH_2)_2OH$ |
| 8 | $TGAC_2$ | $NH_2(CH_2)_3NH(CH_2)_4NH_2$ | $AC_2$ | —H | —M | $—NH(CH_2)_3NH(CH_2)_4NH_2$(1) |
| 9 | $TGAC_2$ | $NH_2(CH_2)_3NH(CH_2)_4NH_2$ | $AC_2$ | —H | —M | $—NH(CH_2)_4NH(CH_2)_3NH_2$(2) |
| 10 | $TGAC_3$ | $NH_2(CH_2)_3NH(CH_2)_4NH_2$ | $AC_3$ | —H | —M | $—NH(CH_2)_3NH(CH_2)_4NH_2$(1) |
| 11 | $TGAC_3$ | $NH_2(CH_2)_3NH(CH_2)_4NH_2$ | $AC_3$ | —H | —M | $—NH(CH_2)_4NH(CH_2)_3NH_2$(2) |
| 12 | $TGAC_{2-5}$ | $NH_2(CH_2)_3NH(CH_2)_2OH$ | $AC_{2,3}$ | —H | —M | $—NH(CH_2)_3NH(CH_2)_2OH$(3) |

TABLE III-continued

| Comp. | Reagents | | End product of formula I | | | |
|---|---|---|---|---|---|---|
| No. | TGAC | Amine | A/AC(*) | B | M(**) | Y |
| 13 | $TGAC_{2-5}$ | $NH_2(CH_2)_3NH(CH_2)_2OH$ | $AC_{4,5}$ | —H | —M | $-NH(CH_2)_3NH(CH_2)_2OH$[3] |
| 14 | $TGAC_{2-5}$ | $NH(CH_2)_3NH(CH_2)_4NH(CH_2)_3NH_2$ | $AC_{2,3}$ | —H | —M | $-NH(CH_2)_3NH(CH_2)_4NH(CH_2)_3NH_2$[4] |
| 15 | $TGAC_{2-5}$ | $NH_2(CH_2)_3NH(CH_2)_4NH(CH_2)_3NH_2$ | $AC_{4,5}$ | —H | —M | $-NH(CH_2)_3NH(CH_2)_4NH(CH_2)_3NH_2$[4] |
| 16 | $TGAC_{2-5}$ | $NH_2(CH_2)_3NH(CH_2)_4NH_2$ | $AC_{4,5}$ | —H | —M | $-NH(CH_2)_3NH(CH_2)_4NH_2$[5] |
| 17 | $TGAC_{2-5}$ | $NH_2(CH_2)_3NH(CH_2)_4NH_2$ | $AC_{4,5}$ | —H | —M | $-NH(CH_2)_4NH(CH_2)_3NH_2$[6] |
| 18 | $TGAC_{1-5}$ | 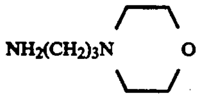 | $AC_{1-5}$ | —H | —M | 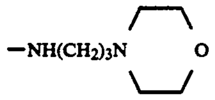 |
| 19 | $TGAC_2$ | $NH_2(CH_2)_2NH(CH_2)_2NH_2$ | $AC_2$ | —H | —M | $-NH(CH_2)_2NH(CH_2)_2NH_2$ |
| 20 | $TGAC_{2-5}$ | $NH_2(CH_2)_3NH(CH_2)_3NH_2$ | $AC_{2-5}$ | —H | —M | $-NH(CH_2)_3NH(CH_2)_3NH_2$ |
| 21 | $TGAC_3$ | $NH_2(CH_2)_3NH(CH_2)_2NH(CH_2)_3NH_2$ | $AC_3$ | —H | —M | $-NH(CH_2)_3NH(CH_2)_2NH(CH_2)_3NH_2$ |
| 22 | $TGAC_1$ | $NH_2(CH_2)_3NH(CH_2)_3NH(CH_2)_3NH_2$ | $AC_1$ | —H | —M | $-NH(CH_2)_3NH(CH_2)_3NH(CH_2)_3NH_2$ |
| 23 | $TGAC_{1-5}$ | $NH_2(CH_2CH_2NH)_4CH_2CH_2NH_2$ | $AC_{1-5}$ | —H | —M | $-NH(CH_2CH_2NH)_4CH_2CH_2NH_2$ |
| 24 | $TGAC_{1-5}$ | 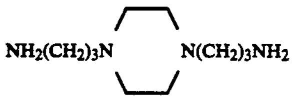 | $AC_{2-5}$ | —H | —M | 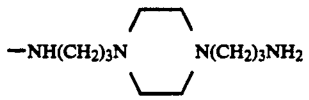 |
| 25 | $TGAC_5$ | 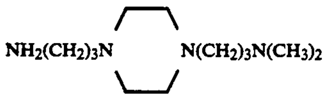 | $AC_5$ | —H | —M | 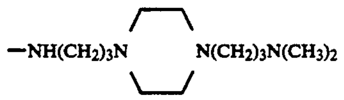 |
| 26 | $TGAC_{4,5}$ | 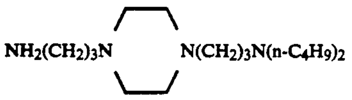 | $AC_{4,5}$ | —H | —M | 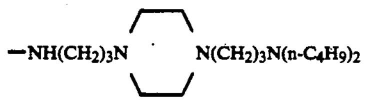 |
| 27 | $TGAC_{2-5}$ | $NH(CH_3)(CH_2)_3NHCH_3$ | $AC_{2-5}$ | —H | —M | $-N(CH_3)(CH_2)_3NHCH_3$ |
| 28 | $TGAC_2$ | $NH(CH_3)(CH_2)_3N(CH_3)_2$ | $AC_2$ | —H | —M | $-N(CH_3)(CH_2)_3N(CH_3)_2$ |
| 29 | $TGAC_4$ | 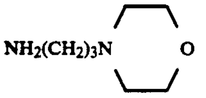 | $AC_4$ | —H | —M | 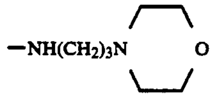 |
| 30 | $TGAC_{2-5}$ | 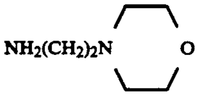 | $AC_{2-5}$ | —H | —M | 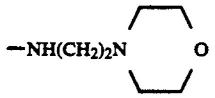 |
| 31 | $TGAC_{1-5}$ | 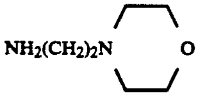 | $AC_{2-5}$ | —H | —M | 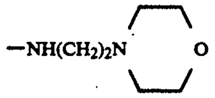 |
| 32 | $TGAC_{2-5}$ | $NH_2(CH_2)_3N[(CH_2)_3NH_2]$ | $AC_{2-5}$ | —H | —M | $-NH(CH_2)_3N[(CH_2)_3NH_2]_2$ |
| 33 | $TGAC_2$ | $NH_2(CH_2)_3N[(CH_2)_3NH_2]_2$ | $AC_2$ | —H | —M | $-NH(CH_2)_3N[(CH_2)_3NH_2]_2$ |

Legenda
(*) $AC_1$ = (Z)-4-decenoyl
$AC_2$ = 8-methylnonanoyl
$AC_3$ = decanoyl
$AC_4$ = 8-methyldecanoyl
$AC_5$ = 9-methyldecanoyl
(**) —M = alpha-D-mannopyranosyl
(1) and (2) The two products simultaneously obtained by reaction of the two different aminogroups are separated during the reverse phase column chromatography.
(3) The product is obtained by carrying out the same procedure for the preparation of compound 2 but separating and pooling together only those fractions of the reverse-phase chromatography that show very close $t_R$ (min.) values when checked by HPLC (instead of pooling together all fractions which contain reaction products of the formula I).
(4) The product is obtained by carrying out the same procedure for the preparation of compound 5 but separating and pooling together only those fractions of the reverse-phase chromatography that show very close $t_R$ (min.) values when checked by HPLC (instead of pooling together all fractions which contain reaction products of the formula I).
(5) The product is obtained by carrying out the same procedure for the preparation of compound 3 but separating and pooling together only those fractions of the reverse-phase chromatography that show very close $t_R$ (min.) values when checked by HPLC (instead of pooling together all fractions which contain reaction products of the formula I).
(6) The product is obtained by carrying out the same procedure for the preparation of compound 4 but separating and pooling together only those fractions of the reverse-phase chromatography that show very close $t_R$ (min.) values when checked by HPLC (instead of pooling together all fractions which contain reaction products of the formula I).

TABLE IIIa

| Yields and equivalent weight (EW) of some representative compounds of formula I. Between brackets are indicated the number of equivalents titrated for each molecule. | | |
|---|---|---|
| Compound No. | Yield % | EW |
| 1 | 43 | 850 (×2) |
| 2 | 49 | 870 (×2) |
| 3 | 27 | 580 (×3) |
| 4 | 29 | 610 (×3) |
| 5 | 61 | 460 (×4) |
| 6 | 52 | 855 (×2) |
| 7 | 47 | 890 (×2) |
| 8 | 28 | 600 (×3) |
| 9 | 25 | 590 (×3) |
| 10 | 31 | 545 (×3) |
| 11 | 23 | 570 (×3) |
| 12 | 27 | 865 (×2) |
| 13 | 39 | 860 (×2) |
| 14 | 23 | 470 (×4) |
| 15 | 37 | 495 (×4) |
| 16 | 18 | 595 (×3) |
| 17 | 37 | 590 (×3) |
| 32 | 32 | 485 (×4) |
| 33 | 36 | 490 (×4) |

TABLE IIIb

| Retention times ($t_R$) determined as described above for some representative compounds of the invention. | |
|---|---|
| Compound No. | $t_R$ (min) |
| 6(1) | 13.8(*) |
| 7(2)(12) | 13.9(*) |
| 8(3) | 15.7(*) |
| 9(4) | 15.7(*) |
| 14(5) | 16.6(**)(*) |
| 13 | 14.3(***) |
| 16 | 18.1(***) |
| 15 | 18.5(***) |
| 33(32) | 16.2(*) |

(*)This value refers also to the component 2 of the mixture reported between the brackets
(**)Value referred to the component 2 of the mixture
(***)Values referred to the component 4 of the mixture TABLE IIIc

| Significant $^1$H-NMR assignments of some representative compounds recorded in DMSO-$d_6$ with tetramethylsilane (TMS) as internal reference (delta = 0.00 ppm). | |
|---|---|
| Compound 1: | 2.17(NCH$_3$); 3.15, 2.32(CH$_2$-polyamine aliphatic chain); 2.02, 1.45, 1.13, 0.82 (aliphatic acyl chain); 4.32-6.09 (peptidic CH's); 6.32-8.62(aromatic protons and peptidic NH's) |
| Compound 2: | 3.23, 2.95, 2.11, 1.58(CH$_2$-polyamine aliphatic chain); 2.04, 1.45, 1.15, 0.84 (aliphatic acyl chain); 3.42(mannose); 4.36-6.13(peptidic CH's); 6.43-8.56 (aromatic protons and peptidic NH's) |
| Compound 3: | 3.31, 2.93, 2.11, 1.58(CH$_2$-polyamine aliphatic chain); 2.04, 1.45, 1.15, 0.82 (aliphatic acyl chain); 4.35-5.75 (peptidic CH's); 6.42-8.42(aromatic protons and peptidic NH's) |
| Compound 4: | 3.31, 2.93, 2.11, 1.58(CH$_2$-polyamine aliphatic chain); 2.04, 1.45, 1.15, 0.82 (aliphatic acyl chain); 4.35-5.75 (peptidic CH's); 6.42-8.42(aromatic protons and peptidic NH's) |
| Compound 5: | 3.29, 2.93, 2.64, 2.08, 1.71, 1.22 (CH$_2$-polyamine aliphatic chain); 2.03, 1.43, 1.18, 0.84(aliphatic acyl chain); 4.32-6.04(peptidic CH's); 6.28-8.62 (aromatic protons and peptidic NH's) |
| Compound 32: | 3.33, 2.82(CH$_2$—N, polyamine); 1.65 (CH$_2$-polyamine aliphatic chain); 2.03, 1.43, 1.22, 0.83(aliphatic acyl chain); 3.45(mannose); 4.12-5.63(peptidic CH's); 6.31-8.53(aromatic protons and peptidic |

TABLE IIIc-continued

| Significant $^1$H-NMR assignments of some representative compounds recorded in DMSO-$d_6$ with tetramethylsilane (TMS) as internal reference (delta = 0.00 ppm). |
|---|
| NH's) |

We claim:

1. A teicoplanin derivative of the formula I:

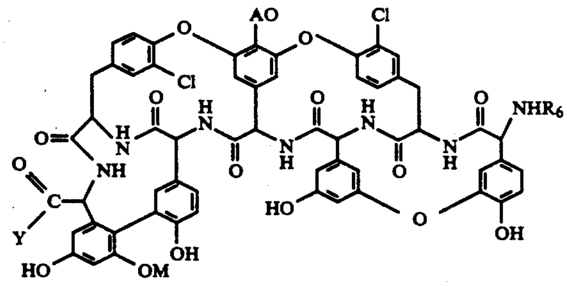

wherein:

A represents N[($C_9$-$C_{12}$)aliphatic acyl]-beta-D-2-deoxy-2-aminoglucopyranosyl;

$R^6$ is hydrogen or a protecting group of the amine function;

M represents alpha-D-mannopyranosyl;

Y represents a di- or poly-amine group of the formula $$—NR—[(CH_2)_mNR^1]_n—X—[(CH_2)_kNR^2]_h—(CH_2)_p—NR^3R^4$$

wherein

R is hydrogen or linear or branched ($C_1$-$C_8$)alkyl;

$R^1$ is hydrogen or linear or branched ($C_1$-$C_8$)alkyl;

$R^2$ is hydrogen or linear or branched ($C_1$-$C_8$)alkyl;

$R^3$ and $R^4$ are each independently hydrogen, linear or branched ($C_1$-$C_8$)alkyl optionally bearing a $NH_2$, OH or SH substituent or taken together with the adjacent nitrogen atom form a 5 to 7 membered saturated heterocyclic ring optionally containing a further —S—, —O— or —$NR^5$— heteroatom selected from pyrrolidine, piperidine, oxazolidine, thiazolidine, isoxazolidine, isothiazolidine, morpholine, piperazine, thiomorpholine, hexahydroazepine, hexahydro-1,5- diazepine and hexahydro-1,4-diazepine wherein the further nitrogen in piperazine, hexahydro-1,5-diazepine and hexahydro-1,4-diazepine is represented by $NR^5$ is hydrogen or $C_1$-$C_4$ alkyl, m, k and p each independently represent an integer from 2 to 8;

n and h, each independently, represent an integer from 0 to 4;

X represents a single bond, or when n is 1, taken together with the adjacent group $NR^1$, it represents a bifunctional radical of the formula:

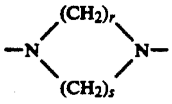 or

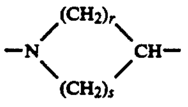

wherein r and s each independently represent an integer from 1 to 6, with the proviso that their sum is an integer from 3 to 8; or an acid addition salt thereof.

2. A compound of claim 1 wherein the ($C_9$–$C_{12}$) aliphatic acyl radical of the moiety represented by the symbol A is: (Z)-4-decenoyl, 8-methylnonanoyl, decanoyl, 8-methyldecanoyl, 9-methyldecanoyl, 6-methyloctanoyl, nonanoyl, 10-methylundecanoyl or dodecanoyl.

3. A compound of claim 2 wherein $R^6$ is hydrogen or a protecting group of the amine function, R, $R^1$ and $R^2$, are hydrogen or linear or branched alkyl radicals of 1 to 4 carbon atoms, $R^3$ and $R^4$ are each independently hydrogen, linear or branched alkyl radicals of 1 to 4 carbon atoms optionally bearing a $NH_2$, OH or SH substituent, or $R^3$ and $R^4$ taken together with the adjacent nitrogen atom represent one of the following rings:

pyrrolidine, piperidine, oxazolidine, thiazolidine, isoxazolidine, isothiazolidine, morpholine, piperazine, thiomorpholine, hexahydroazepine, hexahydro-1,5-diazepine and hexahydro-1,4-diazepine;

$R^5$ is hydrogen or $C_1$–$C_4$ alkyl;

the symbols m, k and p represent integers from 2 to 6;

the symbol n and h represents 0, 1 or 2;

the symbol X represents a single bond or, when n is 1, taken together with the adjacent group $NR^1$ represents a bifunctional radical of the formula

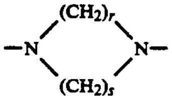
or

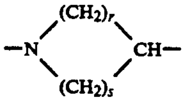

wherein r and s are both 2 or one is 1 and the other is 2 or 3 or a pharmaceutically acceptable acid addition salt thereof.

4. A compound of claim 3 wherein the aliphatic acyl radical of the moiety represented by the symbol A is a ($C_{10}$–$C_{11}$)aliphatic acyl radical selected from: (Z)-4-decenoyl, 8-methylnonanoyl, decanoyl, 8-methyldecanoyl and 9-methyldecanoyl.

5. A compound of claim 4 wherein R is hydrogen or methyl, $R^1$ and $R^2$ are hydrogen, $R^3$ and $R^4$ each independently are hydrogen, a linear or branched alkyl of 1 to 4 carbon atoms optionally bearing a $NH_2$, OH or SH substituent or taken together with the adjacent nitrogen atom represents pyrrolidine, morpholine, or piperazine and $R^5$ is hydrogen or methyl;

the symbols m, k and p represent integers from 2 to 4;

the symbols n and h represent 0 or 1;

the symbol X represents a single bond or when n is 1, taken together with the adjacent group $NR^1$ represents a bifunctional radical of the formula:

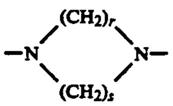

wherein r and s are both 2; or a pharmaceutically acceptable acid addition salt thereof.

6. A compound of claim 1 wherein

A represents N[($C_{10}$–$C_{11}$)aliphatic acyl]-beta-D-2-deoxy-2-aminoglucopyranosyl wherein the ($C_{10}$–$C_{11}$)aliphatic acyl radical is selected from (Z)-4-decenoyl, 8-methylnonanoyl, decanoyl, 8-methyldecanoyl and 9-methyldecanoyl;

$R^6$ is hydrogen or a protecting group of the amine function;

M represents alpha-D-mannopyranosyl;

Y represents a di- or poly-amine group of the formula:

$—NH(CH_2)_3N(CH_3)_2$;
$—NH(CH_2)_3NH(CH_2)_2OH$;
$—NH(CH_2)_3NH(CH_2)_4NH_2$;
$—NH(CH_2)_4NH(CH_2)_3NH_2$;
$—NH(CH_2)_3NH(CH_2)_4NH(CH_2)_3NH_2$;

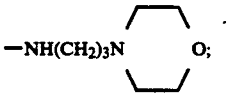

$—NH(CH_2)_2NH(CH_2)_2NH_2$;
$—NH(CH_2)_3NH(CH_2)_3NH_2$;
$—NH(CH_2)_3NH(CH_2)_2NH(CH_2)_3NH_2$;
$—NH(CH_2)_3NH(CH_2)_3NH(CH_2)_3NH_2$;
$—NH(CH_2CH_2NH)_4CH_2CH_2NH_2$; .

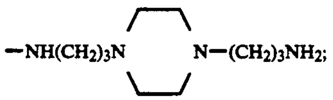

$—N(CH_3)(CH_2)_3NHCH_3$;
$—N(CH_3)(CH_2)_3N(CH_3)_2$;

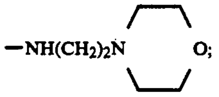

or $—NH(CH_2)_3N[(CH_2)_3NH_2]_2$ or a pharmaceutically acceptable acid addition salt thereof.

7. A compound of claim 6 wherein Y represents
$—NH(CH_2)_3NH(CH_2)_4NH_2$
$—NH(CH_2)_3NH(CH_2)_4NH(CH_2)_3NH_2$ or
$—NH(CH_2)_3N[(CH_2)_3NH_2]_2$ or a pharmaceutically acceptable acid addition salt thereof.

8. A compound of claim 6 wherein the aliphatic acyl radical is 8-methylnonanoyl or decanoyl and Y represents
$—NH(CH_2)_3NH(CH_2)_4NH_2$
$—NH(CH_2)_3NH(CH_2)_4NH(CH_2)_3NH_2$ or
$—NH(CH_2)_3N[(CH_2)_3NH_2]_2$ or a pharmaceutically acceptable acid addition salt thereof.

9. An antibacterial pharmaceutical formulation for treating bacterial infections caused by Group A Streptococci or coagulase negative Staphylococci comprising an effective amount of a compound of claim 1 in admixture with a pharmaceutically acceptable carrier.

10. A method of treating bacterial infections caused by bacteria resistant to glycopeptide antibiotics comprising the vancomycin-ristocetin class, including teicoplanin comprising administering to a patient in need thereof an antibacterially effective amount of a compound of claim 1.

11. A method according to claim 10 wherein the bacteria resistant to glycopeptide antibiotics comprises Enterococci.

12. A method according to claim 11 wherein the Enterococci strains resistant to glycopeptide antibiotics comprises *Enterococci faecalis* or *Enterococci faecium.*

13. A method of treating bacterial infections caused by Group A Streptococci or coagulase negative Staphylococci comprising administering to a patient in need thereof an antibacterially effective amount of a compound of claim 1.

* * * * *